United States Patent [19]

Cochran et al.

[11] Patent Number: 5,039,508
[45] Date of Patent: Aug. 13, 1991

[54] PRODUCTION OF HYDROGEN PEROXIDE

[75] Inventors: Robert N. Cochran, West Chester; Lawrence M. Candela, Philadelphia, both of Pa.

[73] Assignee: ARCO Chemical Technology, Inc., Wilmington, Del.

[21] Appl. No.: 554,770

[22] Filed: Jul. 19, 1990

Related U.S. Application Data

[63] Continuation-in-part of Ser. No. 463,090, Jan. 10, 1990, abandoned, which is a continuation-in-part of Ser. No. 295,409, Feb. 10, 1989, Pat. No. 4,897,252.

[51] Int. Cl.$^5$ .................... C01B 15/026; C07C 45/32
[52] U.S. Cl. ..................................... 423/591; 568/320
[58] Field of Search ......................... 423/591; 568/320

[56] References Cited

U.S. PATENT DOCUMENTS

| | | | |
|---|---|---|---|
| 2,871,102 | 1/1959 | Rust et al. | 423/591 |
| 2,871,103 | 1/1959 | Skinner et al. | 423/591 |
| 2,871,104 | 1/1959 | Rust | 423/591 |
| 3,003,853 | 10/1961 | Mecorney et al. | 423/591 |

FOREIGN PATENT DOCUMENTS 758907 10/1956 United Kingdom ............... 423/591

Primary Examiner—Wayne A. Langel
Attorney, Agent, or Firm—William C. Long

[57] ABSTRACT

Hydrogen peroxide is produced by liquid phase molecular oxygen oxidation of methyl benzyl alcohol, the reaction being carried out such that the oxygen absorption rate is 90% or more of the maximum at the reaction conditions and the exit gas oxygen partial pressure is not greater than 3.0, the minimum necessary to establish the maximum oxygen absorption rate.

2 Claims, 6 Drawing Sheets

PRODUCTION OF HYDROGEN PEROXIDE

RELATED APPLICATIONS

This application is a continuation-in-part of copending application Ser. No. 07/463,090 filed Jan. 10, 1990, abandoned, which in turn is a continuation-in-part of application Ser. No. 07/295,409 filed Feb. 10, 1989, now U.S. Pat. No. 4,897,252.

BACKGROUND OF THE INVENTION

1. Field of the Invention

The present invention relates to the production of hydrogen peroxide by the oxidation of methyl benzyl alcohol.

2. Description of the Prior Art

Hydrogen peroxide is an important chemical of commerce which is produced in very large quantities for use in a number of industrial applications. The predominant process used commercially for the production of hydrogen peroxide involves the oxidation of anthrahydroquinone, extraction of hydrogen peroxide and reduction of the resulting anthraquinone to anthrahydroquinone which is reused. This process requires very high capital expenditures in that use of a working solvent with efficient recycle of various process components is necessary.

Substantial efforts have been directed to processes which involve direct combination of hydrogen and oxygen but thus far such processes have not found widespread success.

Hydrogen peroxide has been formed by the oxidation of secondary alcohols. At one time the production of hydrogen peroxide by oxidation of isopropanol was practiced commercially. Other secondary alcohols which have been mentioned as possible starting materials for hydrogen peroxide production include methyl benzyl alcohol and cyclohexanol. See, for example, U.S. Pat. Nos. 2,871,102–4 of Shell Development.

Hydrogen peroxide has also been formed by oxidation of high boiling secondary alcohols such as diaryl methanol, the product hydrogen peroxide being stripped from the reaction mixture during oxidation; see U.S. Pat. No. 4,303,632.

In certain commercial technologies, substantial quantities of various secondary alcohols are produced. For example, in the coproduction of propylene oxide and styrene monomer by ethylbenzene hydroperoxide epoxidation, methyl benzyl alcohol which is also referred to as alpha phenyl ethanol, 1-phenyl ethanol or methyl phenyl carbinol, is formed and ultimately converted by dehydration to styrene monomer. See U.S. Pat. No. 3,351,635.

The present invention provides a process where commercial streams containing methyl benzyl alcohol can be employed effectively and efficiently for hydrogen peroxide production.

SUMMARY OF THE INVENTION

In accordance with the invention, an improved process for the production of hydrogen peroxide by oxidation of methyl benzyl alcohol is provided. In particular, the process of this invention involves the improved production of hydrogen peroxide by molecular oxygen oxidation of methyl benzyl alcohol in the liquid phase wherein the rate of oxygen absorption in the liquid phase during the reaction is maintained at a level which is at least 90% of the maximum rate at which oxygen can be absorbed at the conditions of the reaction, while at the same time the partial pressure of oxygen in the gases exiting the reaction zone is not more than about 3.0 times the minimum oxygen partial pressure necessary to establish the maximum oxygen absorption rate.

BRIEF DESCRIPTION OF THE DRAWINGS

The accompanying

DETAILED DESCRIPTION OF THE INVENTION

Figure 1:
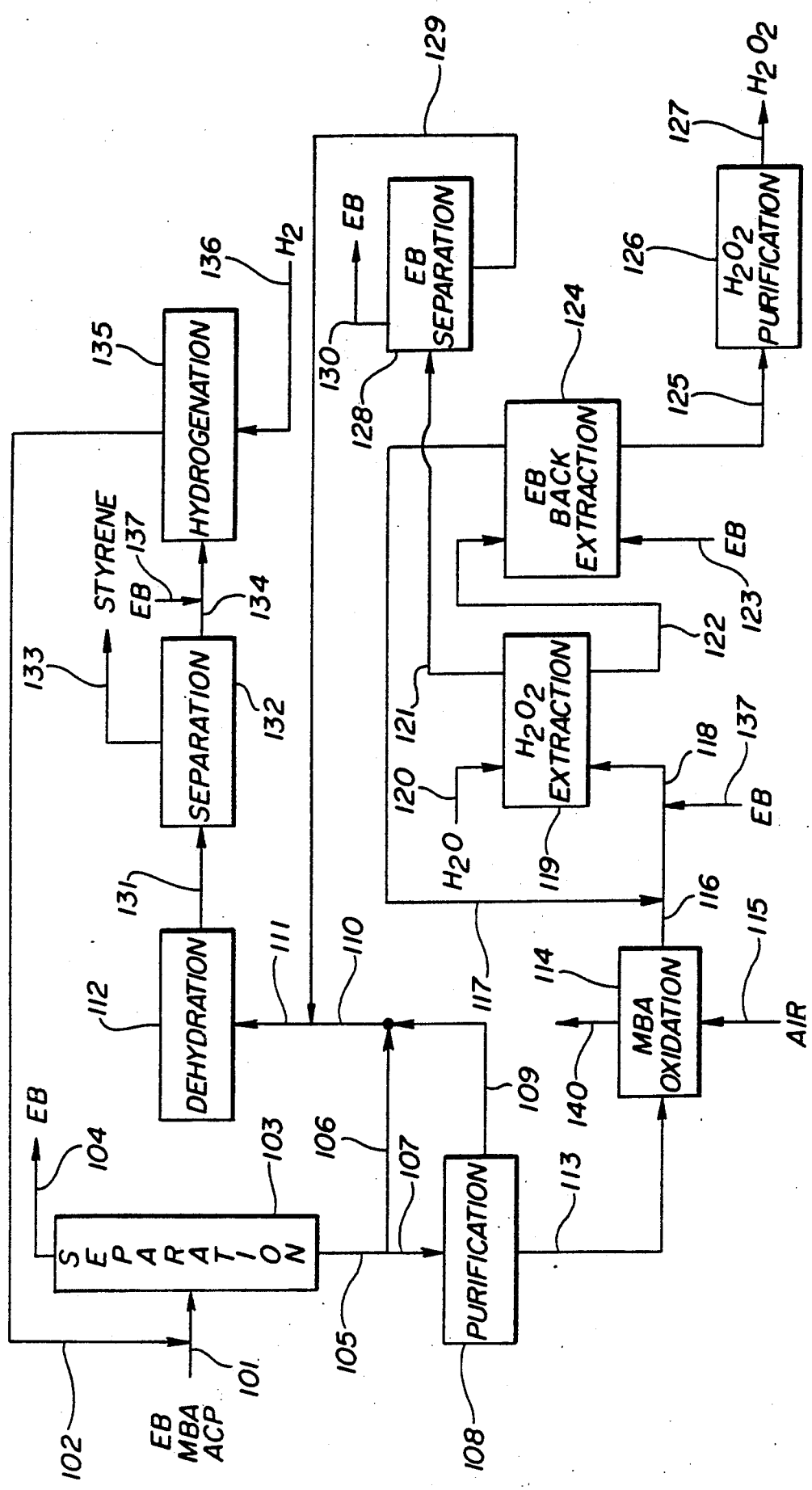
FIG. 1 illustrates in schematic form a suitable embodiment of the invention.

In accordance with the teachings of the prior art, the oxidation of secondary alcohols to produce hydrogen peroxide has been carried out either with water being added to the alcohol feed and/or under conditions of reflux whereby condensibles including water were returned to the reaction mixture and allowed to build up in concentration therein. See Rust U.S. Pat. No. 2,871,104.

As described in U.S. Pat. No. 4,897,252, methyl benzyl alcohol is oxidized in the liquid phase with molecular oxygen at elevated temperatures and pressure with the concentration of water in the reaction mixture maintained below 4% by weight, preferably below 2% by weight and most preferably below 1% by weight. In this way high reaction rates and selectivities to hydrogen peroxide can be achieved.

The oxidation of liquid organic compounds using a gas containing oxygen requires the intimate mixing of the separate gas and liquid phases. If the rate of oxygen transfer between the separate phases is slow compared to the chemical reaction rate, the mass-transfer of the oxygen controls the overall process oxidation rate, and the system is "oxygen-starved". Altering process conditions to enhance the mixing of the two phases, or to increase the amount of oxygen contacting the reacting organic phase, will result in an increase in the process oxidation rate. Such process changes can include increasing the mixing speed or mixing power to a stirred reactor vessel, increasing gas dispersal in the vessel, and increasing oxygen concentration or oxygen partial pressure. By enhancing oxygen mass-transfer, the overall process oxidation rate is increased, until the rate of this mass-transfer becomes fast relative to the intrinsic chemical reaction rate. At this point, the system is "oxygen-sufficient", and the process rate is controlled by the chemical reaction rate. Further increases in such process variables as mixing power or oxygen partial pressure do not result in further increases in the process oxidation rate, and provide a test for oxygen-sufficiency in a given process system. The presence of various impurities in the methyl benzyl alcohol feed also affects the maximum oxygen absorption rate achievable.

In accordance with the present invention, the oxidation of methyl benzyl alcohol to hydrogen peroxide is improved by carrying out the oxidation under conditions such that the rate of oxygen absorption in the liquid reaction phase is at least 90% of the maximum oxygen absorption rate at the reaction conditions employed for the methyl benzyl alcohol being oxidized. It has been found that the characteristics of this particular reaction system are such that unless oxygen absorption rates are near the maximum for the system at the conditions employed, effectiveness of hydrogen peroxide production is dramatically reduced. A further feature of the invention is the partial pressure of oxygen in the gases exiting from the reaction zone must be maintained at a value which is not more than about 3.0 times the minimum exit oxygen partial pressure necessary to achieve the maximum oxygen absorption rate, and preferably not more than 2.0 times this minimum exit oxygen partial pressure. This latter feature is essential in order to avoid the formation of substantial amounts of undesirable by-products.

The oxidant which is used in the present invention is molecular oxygen. Air is a convenient source of the oxygen although pure oxygen, oxygen-enriched air, oxygen diluted with various inerts such as argon, carbon dioxide and the like can be used.

The conditions of temperature and pressure are such as to maintain the reaction mixture in the liquid phase. Elevated temperatures, preferably 120°–180° C., are employed to achieve reasonable reaction rates.

It is important to provide substantial partial pressures of oxygen sufficient to maintain reasonable reaction rates. A preferred range is 15 to 250 psia partial pressure of oxygen in the feed gases, with a broader useful range being 5 to 500 psia.

Total pressure in the reaction zone should be sufficient to maintain the reaction mixture in the liquid phase. Generally, pressures in the range of 50 psig to 1000 psig are useful.

Figure 2:
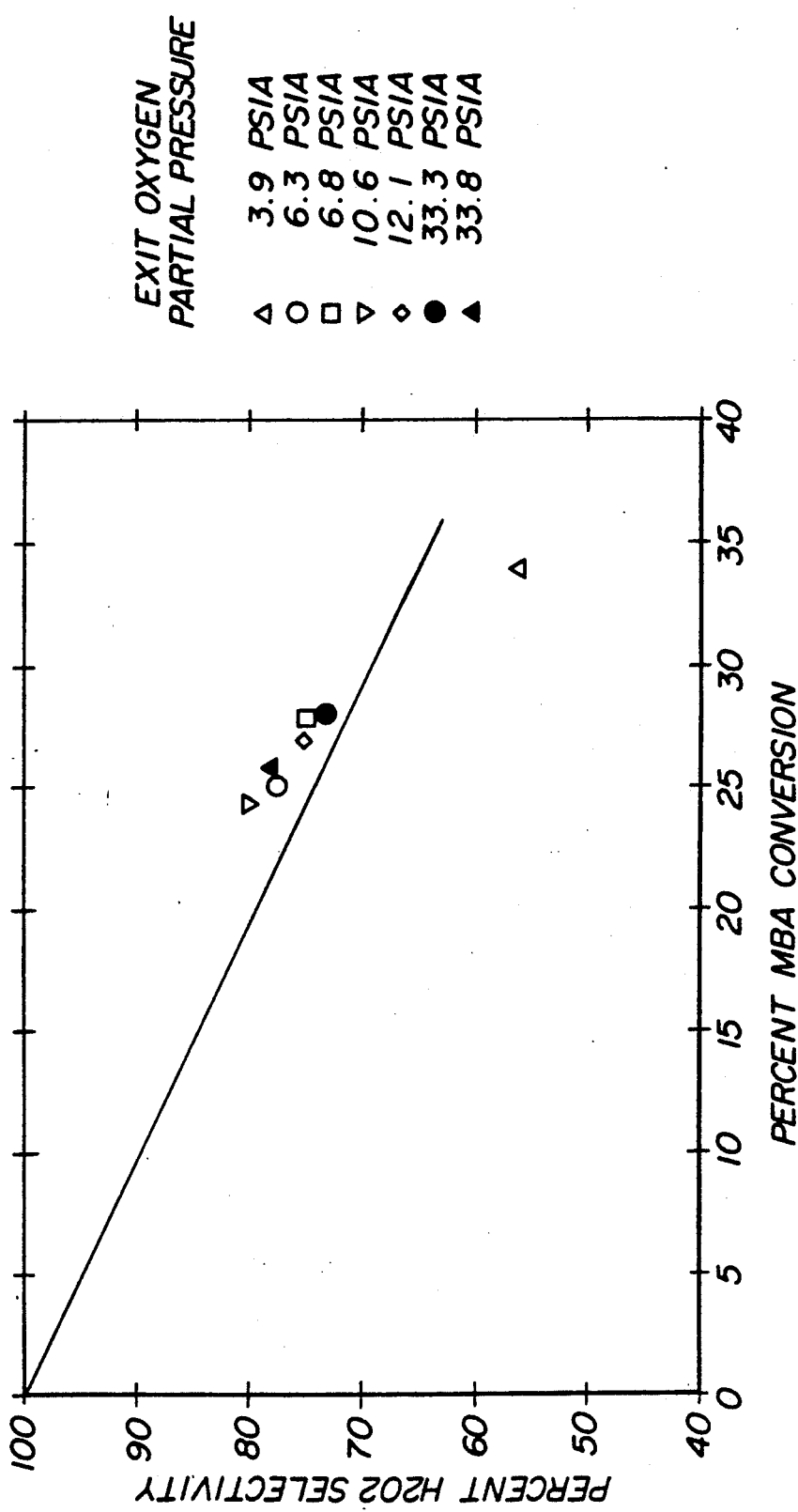
FIG. 2 shows graphically the effect of exit oxygen partial pressure on hydrogen peroxide selectivity.
Figure 3:
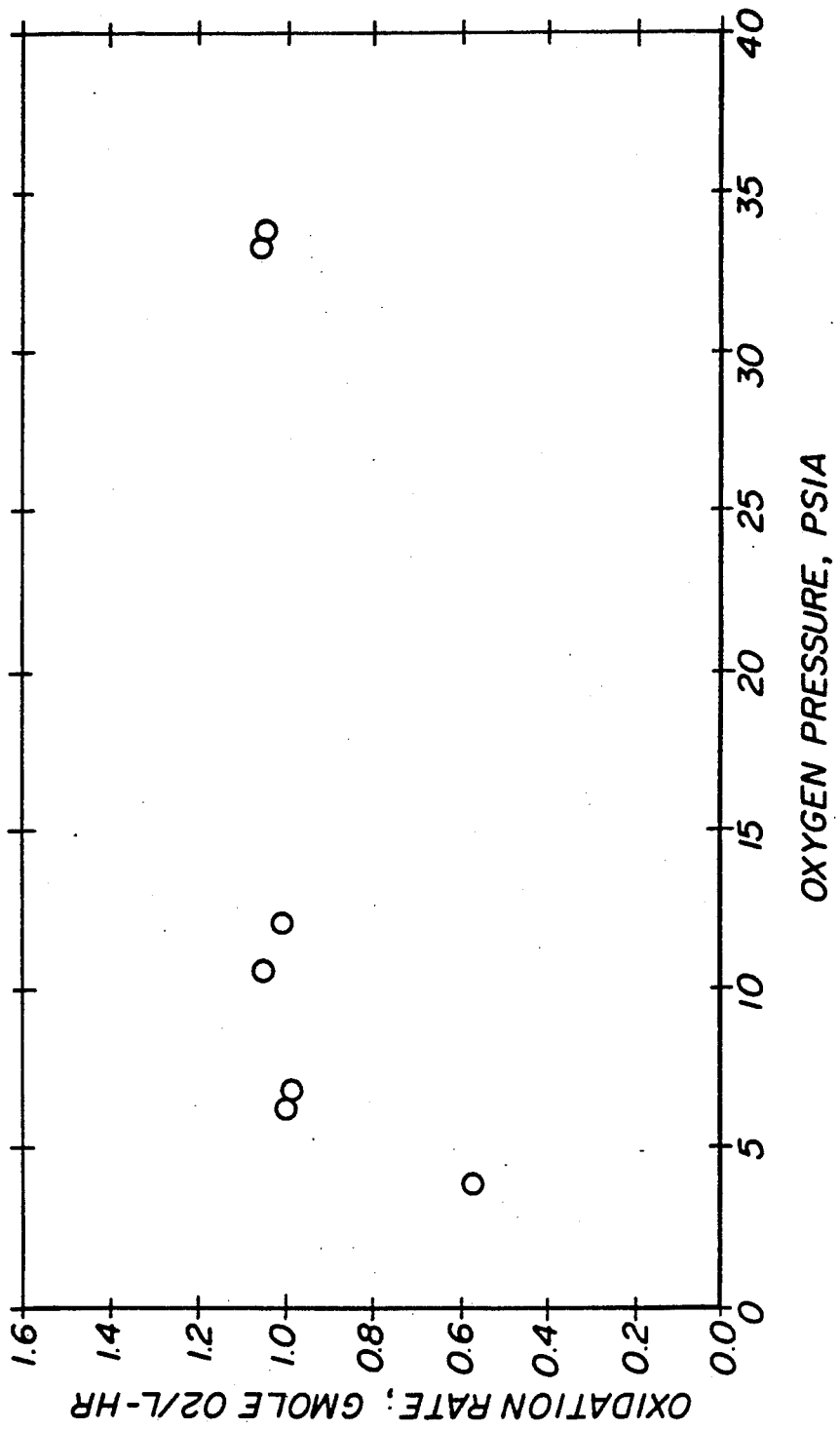
FIG. 3 shows graphically the relation between exit gas oxygen partial pressure and oxygen absorption rate for semibatch operation at 140° C.
Figure 4:
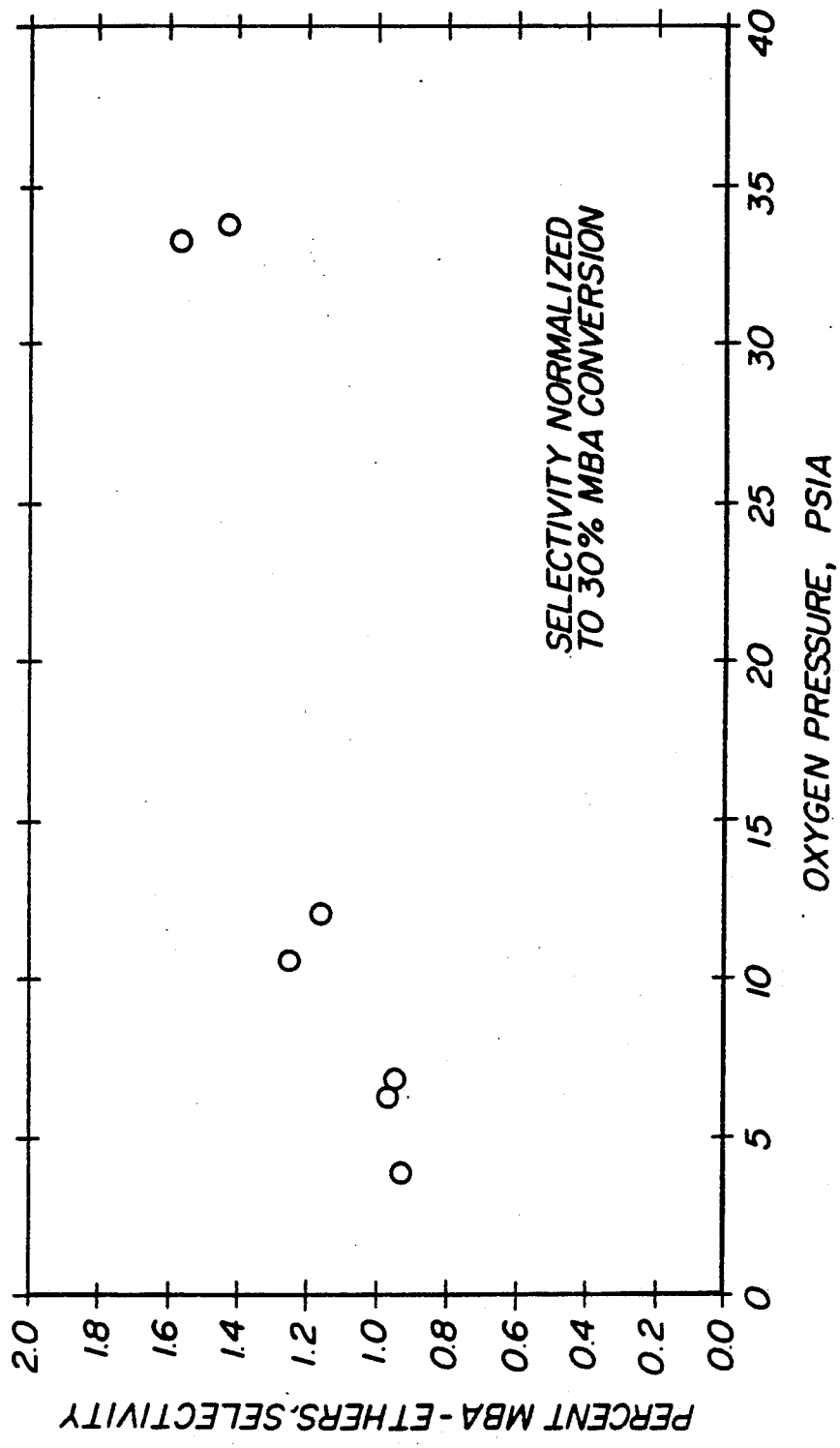
FIGS. 4–6 show graphically the relation between exit gas oxygen partial pressure and selectivity to various by-products for semibatch runs at 140° C.
Figure 5:
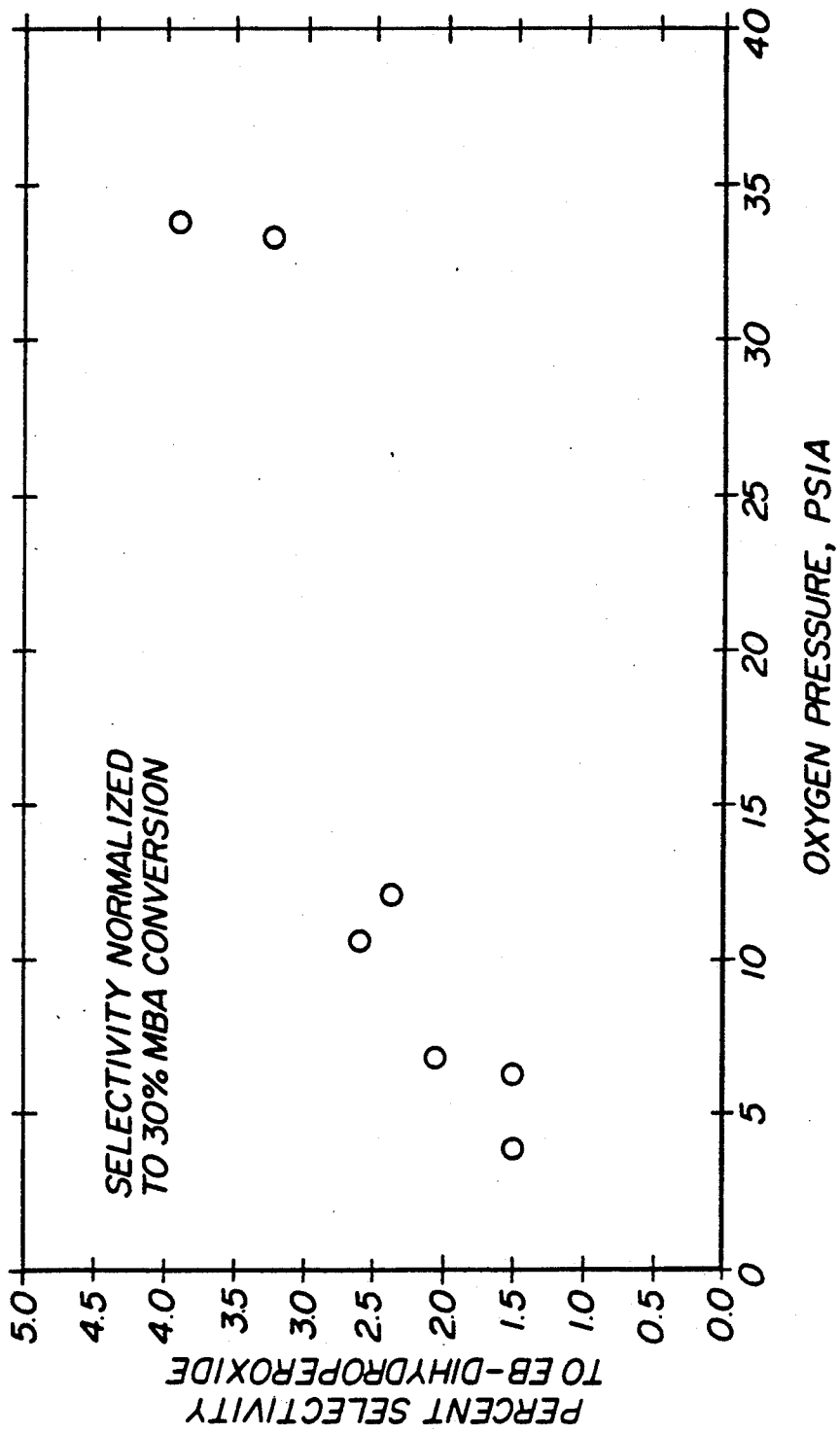
Figure 6:
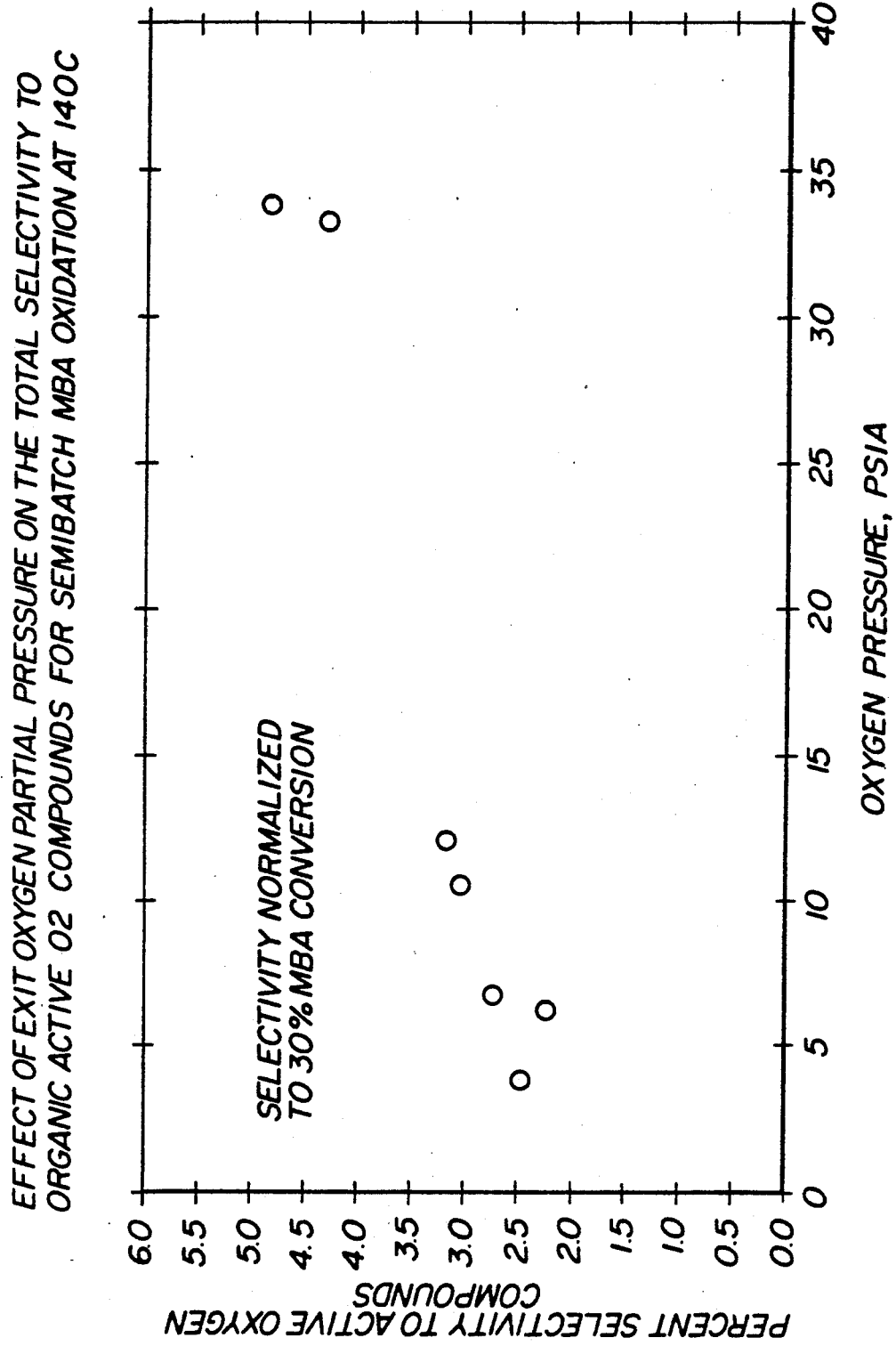

During the reaction, a gas comprised of unreacted oxygen in admixture with other materials is continuously removed from the reaction zone. In order to reach the maximum rate of oxygen absorption at the selected reaction conditions for the methyl benzyl alcohol being oxidized, oxygen partial pressure, mixing and the like are increased as above indicated until there is no further increase in the rate of oxygen absorption. Referring to FIG. 2, it can be seen that once the maximum oxygen absorption rate has been achieved, further increases in oxygen exit gas partial pressure do not further increase oxygen absorption rate or selectivity to hydrogen peroxide. In fact, selectivity to hydrogen peroxide declines somewhat with increasing exit gas oxygen partial pressure above that necessary to achieve the maximum oxygen absorption rate.

It has been found that after the maximum oxygen absorption rate has been achieved, operating at increasing exit gas oxygen partial pressure has a profound effect on the system resulting in substantial increases in the formation of undesirable by-products. This can be seen from FIGS. 3–6.

In accordance with the present invention, the production of such unwanted by-products is minimized by controlling the exit gas oxygen partial pressure to a value which is not more than 3.0 times the exit gas oxygen partial pressure at the maximum oxygen absorption rate, preferably not more than 2.0 times this exit oxygen partial pressure. Usually exit gas oxygen partial pressures of 5 to 15 psia, preferably 5 to 10 psia are appropriate.

It is important that the reaction be carried out at conditions which are outside the flammable region. This is conveniently accomplished by maintaining the concentration of oxygen in the exit gas stream from the reaction zone at less than 14%, and preferably less than 10% by volume of the exit gases.

Metal contaminants and other materials which promote peroxide decomposition are to be avoided in the reaction zone. Known peroxide stabilizers such as pyrophosphates are useful and can be employed.

The oxidation of methyl benzyl alcohol to hydrogen peroxide and acetophenone is an exothermic reaction which requires removal of the heat of reaction. This can be accomplished, for example, by circulating a portion of the reaction mixture through indirect cooling means. Alternatively, the heat can be removed by boil-up and condensation of components of the reaction mixture.

In accordance with this invention, during the liquid phase molecular oxygen oxidation of the methyl benzyl alcohol, the rate of absorption of molecular oxygen in the liquid reaction phase is maintained at 90% or more of the maximum absorption rate at the reaction conditions employed. In order to maintain the necessary high rates of absorption, the oxygen feed rate to the reaction liquid phase must be adequately high. In addition, it is essential that effectively high mass transfer rates between gas and liquid be insured by efficient mixing as by appropriate sparging and/or stirring procedures.

The maximum oxygen absorption rate and the minimum oxygen concentration necessary to achieve this maximum rate can readily be determined by those skilled in the art for a particular set of reaction conditions. An appropriate reaction temperature and pressure is selected as are the feed streams to be employed. A reaction zone having highly efficient sparging and/or stirring means is employed. In the case of semibatch operation, a liquid charge is placed in the reactor and heated to reaction temperature. Oxygen-containing gas is continuously admixed with the liquid, and exit gases are continuously removed from the reaction zone. In such a situation, the rate of oxygen absorption increases with time to a maximum and then declines. By running successive experiments wherein oxygen concentration and/or mixing and gas dispersal are increased, the situation is reached where the oxygen absorption curve remains essentially the same despite such process changes, and the absorption curve then represents the maximum absorption rate expressed as a function of time (or conversion). By conducting further experiments where oxygen concentration as measured by oxygen partial pressure in the exit gas is reduced, the minimum oxygen concentration necessary to maintain the maximum oxygen absorption rate can be determined. In accordance with this invention, the oxygen absorption rate during methyl benzyl alcohol oxidation is maintained at 90% or more of maximum over the course of the semibatch operation and the exit gas oxygen partial pressure is maintained at a value not more than 3.0, preferably not more than 2.0, times the minimum oxygen partial pressure at the maximum oxygen absorption rate.

The situation is somewhat different for the more common continuous oxidation systems, wherein both liquid and molecular oxygen-containing gas are continuously fed to one or more reaction zones and reaction liquid, and offgas is continuously removed. In such procedures, each reaction zone is at steady state conditions, and the oxygen absorption rate for each zone remains essentially unchanged. Of course, in processes employing a plurality of separate zones, each zone has a separate oxygen absorption rate which may be different from the rate in each of the other zones. The maximum absorption rate for each zone is reached when further increases in oxygen concentration and/or mixing and gas dispersal for a particular zone do not result in absorption rate increase. Similarly, the minimum oxygen exit partial pressure can be established at which the maximum oxygen absorption rate for each zone is sustained. It is essential to practice of the invention that the absorption rate for each zone of a continuous system be 90% or more of the maximum rate for that zone and that the exit gas oxygen partial pressure be not more than 3.0, preferably not more than 2.0, times the minimum oxygen partial pressure at the maximum oxygen absorption rate.

The invention can be further described with reference to the attached FIG. 1 which illustrates in schematic form an especially preferred embodiment. Referring to the drawing, a process stream from a commercial process for propylene oxide/styrene monomer coproduction comprised mainly of methyl benzyl alcohol, acetophenone and ethyl benzene in line 101 is combined with a methyl benzyl alcohol stream in line 102 from acetophenone hydrogenation and passed to distillation zone 103.

By conventional distillation ethyl benzene is separated overhead via line 104 for recycle to the propylene oxide/styrene monomer process. A higher boiling stream mainly comprised of methyl benzyl alcohol and acetophenone and containing small amounts of phenol and ethyl phenols is separated from distillation zone 103 through line 105.

A portion of the methyl benzyl alcohol and acetophenone stream passes via lines 106, 110 and 111 to dehydration zone 112. The remaining portion of this stream passes via line 107 to purification zone 108.

It has been found that certain compound such as phenol and ethyl phenols which are usually present with methyl benzyl alcohol in commercial streams severely inhibit the molecular oxygen oxidation of methyl benzyl alcohol to hydrogen peroxide and acetophenone. Accordingly, the methyl benzyl alcohol and acetophenone stream from distillation zone 103 is first treated in purification zone 108 to remove materials which inhibit methyl benzyl alcohol oxidation or to convert these materials to non-inhibitive compounds.

Preferably, purification zone 108 comprises both distillation and caustic and/or ion exchange treatment. By distillation, ethyl phenols can be separated as high boiling material from methyl benzyl alcohol and acetophenone. Basic ion exchange resins such as poly(vinylpyridine) resins can be employed to separate the phenols as described, for example, in Sumitomo Japanese Patent Publication 39025 of 1981. Caustic treatment is effective to remove phenol.

From purification zone 108, the methyl benzyl alcohol/acetophenone stream passes via line 113 to oxidation zone 114 wherein the methyl benzyl alcohol is reacted with molecular oxygen to form hydrogen peroxide and acetophenone. As shown, the molecular oxygen is provided by air introduced via line 115.

Conditions of temperature and pressure and the rates of addition and concentration of the reactants are maintained in zone 114 effective to maintain the oxygen absorption rate in the liquid phase at 90% or more of the maximum oxygen absorption rate. The water content of the reaction mixture is maintained below 4 wt. %, preferably below 2 wt. % and most preferably below 1 wt. % by stripping water formed during the oxidation out of the reaction mixture with unreacted oxygen and inert gases via line 140. Essential to the invention is regulation of oxygen partial pressure in these gases at a value not more than 3.0, preferably not more than 2.0, times the minimum value at the maximum oxygen absorption rate.

In especially preferred practice, reaction zone 114 is comprised of a plurality of separate reaction zones. The liquid reaction mixture is passed in series from one zone to the next while the oxygen-containing gas is introduced in parallel to each of the reaction zones. Each zone is thoroughly back-mixed. Hydrogen peroxide concentration is lowest in the first zone and increases in each successive zone, reaching a maximum in the final zone.

Liquid reaction mixture which contains product hydrogen peroxide passes from 114 via line 116 and is processed for the recovery of the hydrogen peroxide. In an especially preferred practice as described in detail in U.S. Pat. No. 4,897,085, ethyl benzene extraction is used in the separation of the oxidate mixture. The disclosure of patent application is incorporated herein by reference.

The oxidate is admixed with ethyl benzene introduced via line 137 and with an ethyl benzene extraction mixture from back extraction extractor 124 via line 117. The mixture passes to tower extractor 119 and flows countercurrent to water which is introduced via line 120.

The organic phase comprised of ethyl benzene, methyl benzyl alcohol and acetophenone passes via line 122 to distillation zone 128. The aqueous hydrogen peroxide phase passes via line 122 to extractor 124 wherein small amounts of contained methyl benzyl alcohol and acetophenone are extracted with ethyl benzene introduced via line 123. The organic phase is removed via line 117 and recycled to admixture with oxidate from reactor 114.

The aqueous hydrogen peroxide phase passes via line 125 to purification zone 126 from which the final purified hydrogen peroxide is recovered via line 127.

In separation zone 128, ethyl benzene is separated overhead and can be recycled to admixture with oxidate form reactor 114 via lines 130 and 137.

Advantageously, the methyl benzyl alcohol and acetophenone stream passes via line 129 to integration with a commercial propylene oxide/styrene monomer process, as shown. The methyl benzyl alcohol and acetophenone pass via line 129 and are admixed with a comparable stream from separation zone 103 via lines 105, 106 and 110 and passed to dehydration zone 112 wherein methyl benzyl alcohol is dehydrated to styrene monomer. Dehydration effluent is transferred via line 131 to zone 132 wherein product styrene monomer is recovered and removed via line 133.

The remaining mixture of unconverted methyl benzyl alcohol and acetophenone is admixed with ethyl benzene introduced via line 137 and passed via line 134 to zone 135 wherein acetophenone is hydrogenated to methyl benzyl alcohol. The effluent stream from 135 is recycled via 102 to separation zone 103 and thus reintegrated into the process.

The following examples demonstrate the effect of exit oxygen partial pressure on the oxidation rate of methyl benzyl alcohol, on the product selectivity to hydrogen peroxide and on the organic by-product selectivities to various by-products. These data are given graphically in the accompanying FIGS. 2–5. They show that the oxidation rate for the methyl benzyl alcohol feedstock in semibatch tests was constant at about 1.0 gmole $O_2$ absorbed/liter-hr for exit oxygen partial pressure levels between 5 psia and 35 psia, but drops sharply below 5 psia exit oxygen partial pressure. The minimum exit gas oxygen partial pressure necessary to maintain the maximum oxygen absorption rate was about 5 psia. The selectivities to methyl benzyl alcohol ethers, ethylbenzene dihydroperoxide and total organic active oxygen compounds all increase as exit oxygen partial pressure is increased.

COMPARATIVE EXAMPLE A

Oxidation of methyl benzyl alcohol was performed in a one-liter pressure vessel, comprised of grade-1060 aluminum liner, 316 stainless steel casing and high-purity tantalum internals. The reaction was performed semibatch by loading an initial charge of distilled methyl benzyl alcohol, hydrogen peroxide initiator and sodium pyrophosphate stabilizer. The vessel was then pressurized with an air/nitrogen mixture, heated to the desired reaction temperature and the offgas oxygen concentration from the vessel was controlled by continuously varying the air feed. The air/nitrogen mixture used as the oxidant was sparged via diptube to the bottom of the reactor, and agitation was provided by a teflon-coated magnetic stir-bar.

About 670 grams of methyl benzyl alcohol was charged to the reactor along with 10 ppm sodium pyrophosphate stabilizer and 1000 ppm $H_2O_2$ (added as 30% aqueous solution) initiator. The vessel was pressurized to 500 psig with an air/nitrogen mixture comprised of 6.6% $O_2$ and 93.4% $N_2$. The vessel was rapidly heated to 140° C., and the oxygen in the offgas from the vessel was maintained at 6.6% by adjustment of the air feed, giving an offgas oxygen partial pressure or concentration of 33.8 psia. Within 2 hours, oxygen absorption rate increased to a maximum of about 1.05 gmole/liter-hr.

A sample of the final product was analyzed for organic and inorganic composition. The methyl benzyl alcohol conversion was about 25.7%, and the hydrogen peroxide concentration was about 5.2 wt %. $H_2O_2$ selectivity (normalized to 30% methyl benzyl alcohol conversion) was about 74.7%. Organic selectivities (normalized to 30% methyl benzyl alcohol conversion) were 0.24% to phenol, 1.432% to methyl benzyl alcohol ethers, 0.10% to ethylbenzene hydroperoxide, 3.923% to ethylbenzene dihydroperoxide and 4.836% to total organic active oxygen compounds.

COMPARATIVE EXAMPLE B

In another test, conditions of the experiment were identical to Comparative Example A, except that vessel total pressure was held at 500 psig and offgas concentration was controlled at 6.5% giving an offgas oxygen concentration of 33.3 psia. Within 2 hours, oxygen absorption rate increased to a maximum of about 1.06 gmole/liter-hr.

A sample of the final product was analyzed for organic and inorganic composition. The methyl benzyl alcohol conversion was about 28.0%, and the hydrogen peroxide concentration was about 5.3 wt %. $H_2O_2$ selectivity (normalized to 30% methyl benzyl alcohol conversion) was about 71.3%. Organic selectivities (normalized to 30% methyl benzyl alcohol conversion) were 0.31% to phenol, 1.568% to methyl benzyl alcohol ethers, 0.42% to ethylbenzene hydroperoxide, 3.243% to ethylbenzene dihydroperoxide and 4.305% to total organic active oxygen compounds.

EXAMPLE 1

In another test, conditions of the experiment were identical to Comparative Example A, except that vessel total pressure was held at 350 psig and offgas oxygen concentration was controlled at 3.3% giving an offgas oxygen concentration of 12.1 psia. Within 2 hours, oxygen absorption rate increased to a maximum of about 1.01 gmole/liter-hr.

A sample of the final product was analyzed for organic and inorganic composition. The methyl benzyl alcohol conversion was about 27.0%, and the hydrogen peroxide concentration was about 5.3 wt %. $H_2O_2$ selectivity (normalized to 30% methyl benzyl alcohol conversion was about 72.5%. Organic selectivities (normalized to 30% methyl benzyl alcohol conversion) were 0.37% to phenol, 1.160% to methyl benzyl alcohol ethers, 0.22% to ethylbenzene hydroperoxide, 2.383% to ethylbenzene dihydroperoxide and 3.167% to total organic active oxygen compounds.

EXAMPLE 2

In another test, conditions of the experiment were identical to Comparative Example A, except that vessel total pressure was held at 250 psig and offgas oxygen concentration was controlled at 4.0% giving an offgas oxygen concentration of 10.6 psia. Within 2 hours, oxygen absorption rate increased to a maximum of about 1.05 gmole/liter-hr.

A sample of the final product was analyzed for organic and inorganic composition. The methyl benzyl alcohol conversion was about 24.3%, and the hydrogen peroxide concentration was about 5.1 wt %. $H_2O_2$ selectivity (normalized to 30% methyl benzyl alcohol conversion was about 75.4%. Organic selectivities (normalized to 30% methyl benzyl alcohol conversion) were 0.39% to phenol, 1.250% to methyl benzyl alcohol ethers, 0.14% to ethylbenzene hydroperoxide, 2.615% to ethylbenzene dihydroperoxide and 3.046% to total organic active oxygen compounds.

EXAMPLE 3

In another test, conditions of the experiment were identical to Comparative Example A, except that vessel total pressure was held at 250 psig and offgas oxygen concentration was controlled at 2.6% giving an offgas oxygen concentration of 6.8 psia. Within 2 hours, oxygen absorption rate increased to a maximum of about 0.99 gmole/liter-hr.

A sample of the final product was analyzed for organic and inorganic composition. The methyl benzyl alcohol conversion was about 27.9%, and the hydrogen peroxide concentration was about 5.5 wt %. $H_2O_2$ selectivity (normalized to 30% methyl benzyl alcohol conversion was about 73.2%. Organic selectivities (normalized to 30% methyl benzyl alcohol conversion) were 0.41% to phenol, 0.949% to methyl benzyl alcohol ethers, 0.20% to ethylbenzene hydroperoxide, 2.063% to ethylbenzene dihydroperoxide and 2.719% to total organic active oxygen compounds.

EXAMPLE 4

In another test, conditions of the experiment were identical to Example A, except that vessel total pressure was held at 200 psig and offgas oxygen concentration was controlled at 2.9% giving an offgas oxygen concentration of 6.3 psia. Within 2 hours, oxygen absorption rate increased to a maximum of about 1.00 gmole/liter-hr.

A sample of the final product was analyzed for organic and inorganic composition. The methyl benzyl alcohol conversion was about 25.1%, and the hydrogen peroxide concentration was about 5.1 wt %. $H_2O_2$ selectivity (normalized to 30% methyl benzyl alcohol conversion was about 73.2%. Organic selectivities (normalized to 30% methyl benzyl alcohol conversion) were 0.44% to phenol, 0.966% to methyl benzyl alcohol ethers, 0.11% to ethylbenzene hydroperoxide, 1.522% to ehtylbenzene dihydroperoxide and 2.237% to total organic active oxygen compounds.

COMPARATIVE EXAMPLE C

In another test, conditions of the experiment were identical to Example A, except that vessel total pressure was held at 140 psig and offgas oxygen concentration was controlled at 2.5% giving an offgas oxygen concentration of 3.9 psia. Within 2 hours, oxygen absorption rate increased to a maximum of about 0.57 gmole/liter-hr.

A sample of the final product was analyzed for organic and inorganic composition. The methyl benzyl alcohol conversion was about 33.9%, and the hydrogen peroxide concentration was about 5.0 wt %. $H_2O_2$ selectivity (normalized to 30% methyl benzyl alcohol conversion was about 61.4%. Organic selectivities (normalized to 30% methyl benzyl alcohol conversion) were 0.76% to phenol, 0.931% to methyl benzyl alcohol ethers, 0.36% to ethylbenzene hydroperoxide, 1.509% to ehtylbenzene dihydroperoxide and 2.459% to total organic active oxygen compounds.

What is claimed is:

1. The process for the production of hydrogen peroxide which comprises continuously reacting methyl benzyl alcohol in the liquid phase in a plurality of separate back-mixed reaction zones with molecular oxygen at non-flammable reaction conditions, at a temperature in the range 120°–180° C. and a pressure in the range 5 to 1000 psig while maintaining the water content of the liquid reaction mixture below 4 wt. % in each zone, introducing molecular oxygen in parallel into each reaction zone, maintaining the rate at which molecular oxygen is absorbed into the liquid phase in each of the separate zones during the reaction at a value which is at least 90% of the maximum rate at which oxygen can be absorbed at the conditions of the reaction, maintaining the partial pressure of oxygen in the gases exiting each of the separate reaction zones at a value not more than 3.0 times the minimum value necessary to establish the maximum oxygen absorption rate, passing reaction liquid in series from one reaction zone to the next, the concentration of hydrogen peroxide in the reaction liquid increasing in each successive reaction zone.

2. The process of claim 1 wherein the exit gas oxygen partial pressure from each zone is not more than 2.0 times the minimum value necessary to establish the maximum absorption rate for that zone.

* * * * *